US00PP09493P

United States Patent [19]

Zary

[11] Patent Number: Plant 9,493

[45] Date of Patent: Apr. 2, 1996

[54] MINIATURE ROSE PLANT NAMED 'JACWIQ'

[75] Inventor: Keith W. Zary, Thousand Oaks, Calif.

[73] Assignee: Bear Creek Gardens, Inc., Medford, Oreg.

[21] Appl. No.: 386,944

[22] Filed: Feb. 10, 1995

[51] Int. Cl.[6] ..... A01H 5/00

[52] U.S. Cl. ..... Plt./7.1

[58] Field of Search ..... Plt./7.1, 10, 1, Plt./9, 22

[56] References Cited

U.S. PATENT DOCUMENTS

P.P. 6,894 7/1989 Williams ..... Plt./7.1

P.P. 7,448 2/1991 Saville ..... Plt./7.1

*Primary Examiner*—Howard J. Locker

*Attorney, Agent, or Firm*—Klarquist Sparkman Campbell Leigh & Whinston

[57] ABSTRACT

A miniature rose plant characterized by the unique combination of its compact but vigorous, upright habit of growth, its dark green, glossy foliage, its large flower clusters, its dark red-purple fading to lavender flowers, and its ease of propagation from softwood cuttings.

1 Drawing Sheet

The present invention relates to a new and distinct variety of rose plant of the miniature class which was originated by me by crossing the variety SAVawin, U.S. Plant Pat. No. 5,691, with the variety JACsil, U.S. Plant Pat. No. 6,010.

The primary objective of this breeding was to produce a new rose variety having the compact dwarf habit and small flowers of the female parent combined with the glossy foliage, good clustering potential and vigorous growth of the male parent. This objective was substantially achieved, along with other desirable improvements, as evidenced by the following unique combination of characteristics that are outstanding in the new variety and that distinguish it from its parents, as well as from all other varieties of which I am aware:

1. Deep red-purple buds that lighten upon opening;
2. Vigorous growth;
3. Small, dark green, glossy foliage;
4. Production of flowers in large sprays;
5. Compact habit of growth; and
6. Ease of propagation from softwood cuttings.

Asexual reproduction of this new variety by softwood cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—SAVawin, U.S. Plant Pat. No. 5,691.

*Pollen parent.*—JACsil, U.S. Plant Pat. No. 6,010.

Classification:

*Botanical.*—*Rosa hybrida.*

*Commercial.*—Miniature.

FLOWER Observations made from specimens grown in a garden environment at Somis, Calif., in April through November, 1994.

Blooming habit: Continuous.

Bud:

*Size.*—¾ inch long when the petals start to unfurl.

*Form.*—The bud form is short, pointed ovoid.

*Color.*—When sepals first divide, bud color is Red-Purple Group 60A. When half blown, the upper sides of the petals are Red-Purple Group 60A with some color change to Red-Purple Group 63D; and the lower sides of the petals are Red-Purple Group 60A.

*Sepals.*—Color: Green Group 138C. Surface texture: Covered in fine hairs. There are three normally appendaged sepals. There are two unappendaged sepals with hairy edges.

*Receptacle.*—Color: Green Group 138B. Shape: Funnel. Size: Small (3/16 inch by 3/16 inch). Surface: Smooth.

*Peduncle.*—Length: Short (1½ inches to 1¾ inches). Surface: Smooth. Color: Medium green. Strength: Stiff, erect, slender.

Bloom:

*Size.*—Small. Average open size is 2 inches.

*Borne.*—Several together, in pyramidal clusters of 3 to 10 flowers.

*Stems.*—Short, strong. Average length is about 6 to 8 inches.

*Form.*—When first open: High centered. Permanence: Retains its form to the end, outer petals curl back.

*Petalage.*—Number of petals under normal conditions: 25.

*Color.*—The upper side of the petals is Red-Purple Group 60A with some color change to Red-Purple Group 63D. The reverse side of the petals is Red-Purple Group 60A. The base of each petal has a Greenish-White (⅛ inch by ⅛ inch) half moon at the point of attachment. The major color on the upper side is Red-Purple Group 60A.

*Variegations.*—None.

*Discoloration.*—The general tonality at the end of the first day: No change. At the end of the third day:

Gradual change from Red-Purple Group 60A to Red-Purple Group 63D as the flower ages.

*Fragrance.*—Slight.

Petals:

*Texture.*—Thick.

*Shape.*—Round.

*Form.*—Tips slightly recurved, edges slightly quilled.

*Arrangement.*—Imbricated, with few petaloids in the center.

*Persistence.*—Drop off cleanly.

*Lastingness.*—On the plant: Fair (5 to 6 days). As a cut flower: Fair (7 days).

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.

*Styles and stigmas.*—Not present. They appear as a leafy (often called vegetative) tissue tipped in red.

Form: Bush.

Growth: Vigorous, dwarf, upright, branching, and compact. Mature height, without any pruning, is 24 to 30 inches after one full season of growth.

Foliage:

*Number of leaflets on normal mid-stem leaves.*—5.

*Size.*—Small (3 to 3½ inches by 1½ to 1¾ inches).

*Quantity.*—Abundant.

*Color.*—New foliage: Greyed-Red 178A (both sides). Old foliage: Upper: Green Group 139A. Lower: Green Group 139C.

Leaflets:

*Shape.*—Pointed oval.

*Texture.*—Upper side: Leathery, glossy.

*Edge.*—Serrated.

*Serration.*—Single.

*Petiole rachis.*—Color: Green.

*Petiole underside.*—Smooth.

*Stipules.*—Short (¼ inch) serrated, bearded.

*Disease resistance.*—Resistant to mildew and rust under normal growing conditions at Somis, Calif.

Wood:

*New wood.*—Color: Reddish but rapidly turning green. Bark: Smooth.

*Old wood.*—Color: Green. Bark: Smooth.

Prickles:

*Quantity.*—On main canes from base; Ordinary. On laterals from main canes: Ordinary.

*Form.*—Short (5/16 inch), straight to hooked slightly downward.

*Color when young.*—Red.

Small prickles

*Quantity.*—On main stalks: None. On laterals: None.

I claim:

1. A new and distinct variety of rose plant of the miniature class, substantially as herein shown and described, characterized particularly as to novelty by the unique combination of its compact but vigorous, upright habit of growth, its dark green, glossy foliage, its lower flower clusters, its dark red-purple fading to lavender flowers, and its ease of propatation from softwood cuttings.

* * * * *

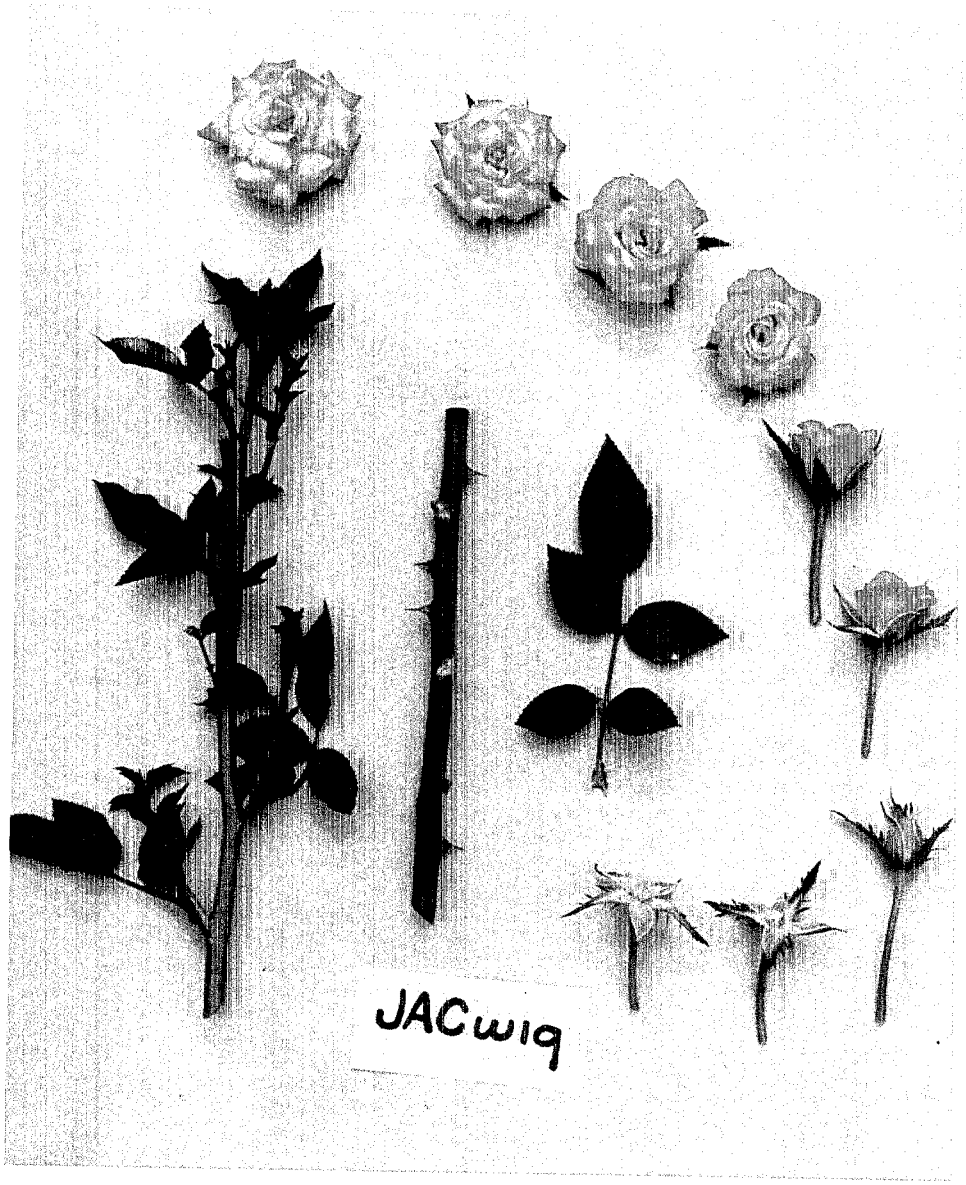
JACw19